(12) United States Patent
Annan et al.

(10) Patent No.: US 6,270,748 B1
(45) Date of Patent: Aug. 7, 2001

(54) CONTRAST ENHANCING AGENT HAVING A POLYMERIC CORE AND POLYMERIC SHELL

(75) Inventors: Nikoi Annan, Willow Grove; Charles Howard Reynolds, Lansdale; Steven Howard Shaber, Horsham; Eric Jon Langenmayr, Bryn Mawr, all of PA (US)

(73) Assignee: Rohm and Haas Company, Phila, PA (US)

( * ) Notice: Subject to any disclaimer, the term of this patent is extended or adjusted under 35 U.S.C. 154(b) by 0 days.

(21) Appl. No.: 09/484,619

(22) Filed: Jan. 18, 2000

Related U.S. Application Data
(60) Provisional application No. 60/116,354, filed on Jan. 19, 1999.

(51) Int. Cl.⁷ .............................. A61B 5/055; A61K 51/00
(52) U.S. Cl. ..................................... 424/9.322; 424/9.323; 424/9.4
(58) Field of Search ..................................... 424/9.3, 9.32, 424/9.322, 9.323, 9.36, 9.4, 9.41, 9.411, 1.21, 1.25, 1.29, 1.33, 1.37

(56) References Cited

U.S. PATENT DOCUMENTS

| | | |
|---|---|---|
| 4,804,529 | 2/1989 | Bardy et al. . |
| 4,880,008 | 11/1989 | Lauffer . |
| 4,899,755 | 2/1990 | Lauffer et al. . |
| 4,986,980 | 1/1991 | Jacobsen . |
| 5,045,304 | 9/1991 | Schneider . |
| 5,122,363 | 6/1992 | Balkus et al. . |
| 5,143,716 | 9/1992 | Unger . |
| 5,250,672 | 10/1993 | Sadler et al. . |
| 5,277,896 | 1/1994 | Balkus . |
| 5,336,762 | 8/1994 | Ranney et al. . |
| 5,358,702 | * 10/1994 | Unger ........................................ 424/9 |
| 5,512,268 | 4/1996 | Grinstaff et al. . |
| 5,534,241 | 7/1996 | Torchilin et al. . |

FOREIGN PATENT DOCUMENTS

| | | |
|---|---|---|
| 409351 A1 | 1/1991 | (EP) . |
| WO91/01147 | 2/1991 | (WO) . |
| WO95/24184 | 9/1995 | (WO) . |
| WO98/28258 | 7/1998 | (WO) . |

OTHER PUBLICATIONS

Aldersberg, et al., "Redistribution and Elimination of Intravenously Injected Particles in Mice", *J. Reticuloendothelial Soc.*, 6, 536–560 (1969).

Singer, et al., "Radiolabeled Latex Particles in the Investigation of Phogocytosis in Vivo: Clearance Curves and Histological Observations", *J. Reticuloendothelial Soc.*, 6, 561–589 (1969).

Goldstein, et al., "Contrast Media for Magnetic Resonance Imaging", Ch. 28, Annual Reports in Medicinal Chemistry–24, Academic Press, 1989.

Tart, et al., "Enteric MRI Contrast Agents: Comparative Study of Five Potential Agents in Humans", *Magnetic Resonance Imaging*, vol. 9, pp. 559–568, 1991.

Wang, et al., "A Kinetic Investigation of the Lanthanide DOTA Chelates. Stability and Rates of Formation and of Dissociation of a Macrocylic Gadolinium II) Polyaza Polycarboxylic MRI Contract Agent", *Inorg. Chem.*, 1991, 31, 1095–1099.

Braybrook, et al., "Synthesis and evaluation of paramagnetic particulates as contract agents for magnetic resonance imaging (MRI)", *Polym. Int.* 1991, 26,251–9.

Aime, et al., "Trends in NMR Studies of Paramagnetic Gd(III) Complexes as Potential Contrast Agents in MRI". *Mag. Res. Imag.*, vol. 9, 843–847, 1991.

King, et al., "Paramagnetic Oil Emulsions as Oral Magnetic Resonance Imaging Contrast Agents", *Mag. Res. Imag.*, vol. 8, 589–598, 1990.

Chang, "Lanthanide magnetic resonance imaging contrast agents: thermodynamic, kinetic, and structural properties of lanthanide (III) macrocyclic complexes", *Eur. J. Solid State Inorg. Chem. 28*, 1991, 237–244.

Meldru, et al., "Magnetoferritin: In Vitro Synthesis of a Novel Magnetic Protein", *Science*, vol. 257, Jul. 24, 1992, 522–523.

Jurisson, et al., "Coordination Compounds in Nuclear Medicine", *Chem. Rev.*, 1993, 93, 1137–1156.

Spirlet, et al., "The gadolinium (III) chelate of 1–oxa–4,7, 10–triazacyclododecane–4,7,10–triacectic acid. Formation of polymeric chains in the solid state and relaxivity properties", *J. Chem. Soc., Dalton Trans . . .* , 1997, 497–500.

* cited by examiner

Primary Examiner—Michael G. Hartley
(74) Attorney, Agent, or Firm—Jeffrey H. Rosedale

(57) ABSTRACT

The present invention pertains to an image enhancing agent having a polymeric core including an image-enhancing compound chemically bound thereto and a polymeric shell surrounding the core and compound. The agent may be used for enhancing MRI images, by introducing gadolinium or other appropriate material into the core. Generally, the core is formed from an acid monomer and an esterified monomer. Preferably, a cross-linking monomer is included in the core.

10 Claims, No Drawings

CONTRAST ENHANCING AGENT HAVING A POLYMERIC CORE AND POLYMERIC SHELL

This is a nonprovisional application of prior pending provisional application Ser. No. 60/116,354 filed Jan. 19, 1999.

This application relates to image contrast enhancing agents for magnetic resonance imaging (MRI) or x-ray.

Imaging, whether x-ray or magnetic resonance, is a well-known and commonly used medical diagnostic technique. In the case of X-ray imaging, an x-ray sensitive film is placed behind an object under study, and the object is bombarded with x-rays. The film is then developed and reveals an image (usually a negative image showing white x-ray-opaque structures on a black background). In some instances, it may be difficult to identify and inspect different structures in the human body through x-ray imaging since many structures are x-ray transparent or translucent and faintly represented structures over-lie one another, obscuring the resulting image. Accordingly, it has become commonplace to introduce x-ray image enhancing agents prior to x-ray diagnosis. The two most common types of x-ray contrast agents are barium salts and a large class of halogenated agents. Barium salts are typically used exclusively for imaging the gastrointestinal tract. Halogenated agents are used to image a variety of areas of the body including the liver, spleen, kidneys, bile-duct, and major arteries such as those found near the heart. Essentially any organic compound substituted with bromine, or especially iodine, will significantly attenuate x-rays leading to improved contrast with respect to surrounding tissue.

In MRI, an image of an organ or tissue is obtained by placing a subject in a strong magnetic field and observing the interactions between the magnetic spins of the protons in the subject and radio frequency electromagnetic radiation. After bombardment with RF energy, the protons undergo relaxation. Relaxation is the process whereby nuclear magnetization returns to its resting state following a perturbation, such as by a radio frequency pulse. Magnetic resonance is characterized by three forms of relaxation, $T_1$ (longitudinal or spin-lattice) relaxation, $T_2$ (transverse or spin-spin) relaxation, and $T_2^*$ relaxation. We are most concerned here with $T_1$ and $T_2$ which are of primary importance in the generation of the image. Magnetic resonance imaging is a complicated but well-known procedure to those skilled in the art and will not be set forth here.

$T_1$ and $T_2$ differ in different tissues in the body and depend on the chemical and physical environment of protons in various organs or tissues. The use of MRI to differentiate between healthy and diseased tissues is most successful in areas of the body where the relaxation times ($T_1$ and $T_2$) of adjacent tissues is varied. For instance, the relaxation times of protons in cerebral spinal fluid and cerebral tissue are quite different, and images resulting from the use of MRI normally possess high contrast. However, in other areas of the body, the relaxation times of the protons in different tissues may be similar. Such areas may be difficult to successfully image, and the MRI image obtained may lack definition and clarity.

Without contrast agents, MRI provides a means of making definitive diagnoses noninvasively. Nevertheless, it has been found that the addition of contrast agents in many cases improves the sensitivity and/or specificity of this imaging technique. In areas of the body where adjacent tissues have similar proton relaxation times, such agents may be preferentially attracted to one of the two similar tissues, changing the proton-relaxation time for that tissue and leading to a high contrast MRI image.

MRI image enhancing agents generally fall into one of three categories: paramagnetic, ferromagnetic, and superparamagnetic. These agents affect the properties of contacted water molecules, thereby enhancing the tissue contrast and improving the diagnostic capability of MRI. A wide range of compounds in all categories have already been investigated. However, few compositions have both the efficacy and the non-toxicity required for extensive use in humans.

Ferromagnetic materials generally contain iron, nickel, and/or cobalt. These materials include magnets, and various objects one might find in a patient, such as aneurysm clips, parts of pacemakers, shrapnel, etc. These materials have a large positive magnetic susceptibility, i.e., when placed in a magnetic field, the field strength is much stronger inside the material than outside. Ferromagnetic materials are also characterized by being made up of clusters of $10^{17}$ to $10^{21}$ atoms called magnetic domains, that all have their magnetic moments pointing in the same direction. The moments of the domains are random in unmagnetized materials, and point in the same direction in magnetized materials. The ability to remain magnetized when an external magnetic field is removed is a distinguishing factor of ferromagnetic materials when compared to paramagnetic, superparamagnetic, and diamagnetic materials. Diamagnetic materials are not used as contrast enhancing agents. In MRI images, ferromagnetic materials cause susceptibility artifacts characterized by loss of signal and spatial distortion. This can occur with even fragments too small to be seen on plain x-ray. This is a common finding in a cervical spine MRI post anterior fusion.

Diamagnetic materials have no intrinsic atomic magnetic moment, but when placed in a magnetic field weakly repel the field, resulting in a small negative magnetic susceptibility. Materials like water, copper, nitrogen, barium sulfate, and most tissues are diamagnetic. The weak negative magnetic susceptibility contributes to the loss of signal seen in bowel on MRI after administration of barium sulfate suspensions.

Superparamagnetic materials consist of individual domains of elements that have ferromagnetic properties in bulk. Their magnetic susceptibility is between that of ferromagnetic and paramagnetic materials. Examples of superparamagnetic materials include iron-containing contrast agents for bowel, liver, and lymph node imaging.

Paramagnetic materials include oxygen and ions of various metals like Fe, Mg, and Gd. These ions have unpaired electrons, resulting in a positive magnetic susceptibility. The magnitude of this susceptibility is less than one one-thousandth of that of ferromagnetic materials. The effect on MRI is an increase in the $T_1$ and $T_2$ relaxation rates (decrease in the $T_1$ and $T_2$ times). Gd is used as an MRI contrast agent. At the proper concentration, Gd contrast agents cause preferential $T_1$ relaxation enhancement, causing increase in signal on $T_1$-weighted images. At high concentrations, as is sometimes seen in the urinary bladder, loss of signal is seen instead, a result of the $T_2$ relaxation effects dominating.

Paramagnetic metal ions suitable as MR contrast agents are all potentially toxic when injected IV at or near doses needed for clinical imaging. With chelation of these ions, acute toxicity is reduced and elimination rate is increased thereby reducing the chance of long term toxicity. One of the more studied complexes is gadolinium diethylenetriamine pentaacetate chelate (GdDTPA). The gadolinium in the chelate contributes a large number of unpaired electrons and consequent large magnetic moment. Enhancement of the relaxation rate of water increases with an increasing number of unpaired electrons, making this an effective MRI image enhancing compound. GdDTPA has proven useful in the imaging of the brain by virtue of its inability to pass through the blood brain barrier. It is quite effective for illuminating lesions of the brain because these lesions compromise the blood-brain barrier allowing the contrast to infiltrate the lesion preferentially over the remainder of the brain.

However, GdDTPA lacks site specificity. When introduced into the vascular system, GdDTPA diffuses throughout the organs and muscular system. Thus, large quantities of contrast agent are usually required to produce adequate contrast. This is particularly problematic for efforts to image the blood pool. Consequently, differentiation among different tissues decreases significantly with time, as the material diffuses.

Accordingly, there remains a need for a safe and efficacious contrast-enhancing agent which does not diffuse through the body and can be made site specific, but is eliminated by the body after its useful life.

SUMMARY OF THE INVENTION

The present invention pertains to an image enhancing agent having a polymeric core including an image-enhancing compound chemically bound thereto and a polymeric shell surrounding the core and compound. The agent may be used for enhancing MRI images, by introducing gadolinium or other appropriate material into the core. Generally, the core is formed from an acid monomer and an esterified monomer. Preferably, a cross-linking monomer is included in the core.

DETAILED DESCRIPTION OF THE INVENTION

It has now been found that by incorporating a suitable metal into a polymer matrix core and encapsulating the resulting composite in an outer shell, a contrast agent can be produced which has good selectivity and contrast, and low toxicity. The particle shell is designed to optimize the pharmacokinetic properties of the particle including biodistribution and bioavailability, and to allow the targeting of specific organs, regions of the body, or cell lines. The particles are synthesized in such a way that the particle size and surface characteristics can be precisely controlled and the particle size distribution can be very narrow.

The metal-loaded nanoparticles of the present invention are generally less than 1 $\mu$ in diameter and have a polymeric core. The polymeric core can be designed to have a high affinity for metals, including gadolinium. A simple example is a core consisting of a large fraction of acrylic acid (AA) or methacrylic acid (MAA) monomers. This core material is complexed with a suitable image-enhancing compound. The core polymer with the image-enhancing compound is surrounded by a polymeric shell. The shell sequesters the image-enhancing compound in the core, preventing leaching and interaction with the patient. The shell can also be functionalized to promote specific interactions with tissues, making the agent tissue specific. The type of functionalization will vary with the tissue to be studied.

The composition of the core and shell can be varied widely depending on the desired final characteristics. In the case of MRI, the core polymer is loaded with any suitable paramagnetic metal, preferably Gd. In the case of x-ray imaging, the core polymer can be loaded with an x-ray-opaque material such as polyiodinated or -brominated liquids or polymers, and inorganic materials such as barium sulfate or other metals. In all cases, the core contains a metal or halogenated material that improves contrast, while the shell is optimized to sequester the core material and provide surface properties that provide for optimum target specificity and bioelimination.

For the contrast enhancing agents of the present invention, the core is generally formed from emulsion polymerization of mixtures of certain Specific monomers selected from the following compounds:

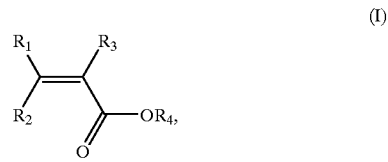

(I)

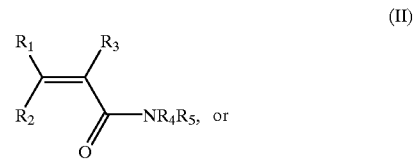

(II)

(III)

wherein:

$R_4$, is selected from the group consisting of H, $C_1$–$C_{12}$ alkyl, $C_1$–$C_{12}$ alkenyl, $C_3$–$C_7$ cycloalkyl, substituted phenyl, heterocyclic, arylalkyl, and $COCR_6$=$CR_7R_8$.

$R_1$, $R_2$, $R_3$, $R_5$, $R_6$, $R_7$, and $R_8$ are each independently selected from the group consisting of H, $C_1$–$C_{12}$ alkyl, $C_1$–$C_{12}$ alkenyl, $C_3$–$C_7$ cycloalkyl, substituted phenyl, heterocyclic, and arylalkyl, and when $R_4$=H in formula I, $R_1$, $R_2$, and $R_3$ are further selected from cyano and halogens; and $R_9$ is selected from the group consisting of H, aryls, phenyls, acetate, $C_1$–$C_4$ alkyl, $C_1$–$C_4$ alcohols, and halo.

In Formula I, when $R_4$ is H, $R_3$ can also be CN or ($C_1$–$C_4$) alkyl sulfonate.

It should be noted that when the compound of formula I is selected and $R_4$ $COCR_6$=$CR_7R_8$ formula 1 becomes the anhydride:

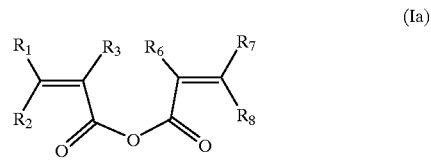

(Ia)

Preferably $R_1$=$R_2$=$R_7$=$R_8$=H and $R_3$=$R_6$=$CH_3$, making:

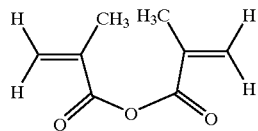

The monomers used to produce the core are preferably selected from acrylic acid, methacrylic acid (MA), methyl methacrylate (MA), styrene (ST), ethyl acrylate (EA), butyl acrylate (BA), 2-ethylhexyl acrylate (EHA), dimethylaminoethyl methacrylate (DMAEMA), tert-butylaminoethyl methacrylate (TBAEMA), hydroxyethyl methacrylate (HEMA), and hydroxypropyl methacrylate (HPMA).

In each case, an acid monomer (such as methacrylic acid) and an ester should be used to prepare the polymeric core of the material of the present invention. When forming cores for loading with a metal such as gadolinium, it is preferable to make the cores as acidic as possible. An acidic core is preferred because, once the core is formed, the acidic regions can be deprotonated to leave binding sites for the metal. A higher content of acid functionality leads to increased numbers of binding sites. However, this must be balanced since if the core is too acidic, a stable emulsion for polymerization cannot be achieved.

The process for preparing the cores is as follows. First, a monomer emulsion in water is formed. This emulsion consists of a mixture of at least one acid monomer, at least one esterified monomer, and a crosslinking agent. Generally the monomer mixture used to produce the core of the material of the present invention is between 10 and 90% acid monomer (such as methacrylic acid), and 10 to 90% of an esterified monomer (such as ethyl acrylate). Preferably, 50–70% acid and 30–50% ester is used, and more preferably 50–60% acid and 40–50% ester. All percentages used herein are calculated on the basis of weight unless otherwise specified. To this is added up to 10% of any suitable crosslinking agent, such as allyl methacrylate (ALMA). Preferably, 1–5% crosslinking agent is used. This is added to sufficient water to produce a mixture having a solids content below 60% on a weight basis, preferably 15–35%.

Although any suitable crosslinking agent may be used in the present invention, crosslinking agents which are preferred for use with the present invention include allyl methacrylate (ALMA), ethylene glycol dimethacrylate (EGDMA), trimethylolpropane trimethacrylate (TMPTMA), divinyl benzene (DVB), glycidyl methacrylate, 2,2-dimethylpropane 1,3 diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, trimethylolpropane triacrylate, trimethylolpropane trimethacrylate, pentaerythritol triacrylate, trimethylolpropane triethoxy triacrylate, glyceryl propoxy triacrylate, pentaerythritol tetraacrylate, pentaerythritol tetramethacrylate, and dipentaerythritol monohydroxypentaacrylate.

It should be noted that, although 10% acid monomer may be used to form the core, as set forth above, the use of such a small amount of an acid monomer will only be successful if the core is subsequently loaded with a metal which is useful at very low loadings. The core, once produced, is loaded with metal by loading the metal into deprotonated areas where acid functionality existed. A higher percentage of acid in the original monomer mix will lead to a greater number of sites available for loading of metal. Accordingly, it is desirable to use greater amounts of acid functional monomer in the original monomer mixture. The limitation is that if the core is too acidic, it cannot be stabilized and the emulsion will gel during polymerization, and no useful material will result. This can be combated, to a limited extent, by adding more water to the starting mixture, but this is only partially successful. Thus a higher acid core (around 70%) will require an emulsion with a lower solids content (nearer to the 15% solids content set forth above), while a lower acid core may be able to be formed using a solids content nearer to 60%.

Once the monomer emulsion is formed, part of the emulsion is removed and combined with more deionized water. This new emulsion mixture is used to make seed to polymerize the main emulsion. To this seed emulsion mixture is added an initiator, such as ammonium persulfate. The amount of this initiator used is important to the properties of the resulting polymer. The greater the amount of initiator used, the more smaller particles are formed. If a smaller amount of initiator is used, the resulting polymerized mixture will contain fewer, larger particles. Generally the amount of initiator to be used should be in the range of 0.05 to 0.2% of seed emulsion. This depends both on the desired final particle size, and on the concentration of the emulsion used. The use of more initiator to make more, smaller, seeds will lead to the formation of more, smaller, particles when the main portion of the emulsion is polymerized. This must be balanced against the amount of material drawn off for seed formation, where a greater amount drawn off will lead to smaller particles being formed in the main polymerization step. In most instances, between 3 and 30% of the original emulsion will be use to produce seed. Preferably, 5–15% will be used. The initiator is prepared as a solution in water. The amount of water used is not critical, but should be sufficient to allow the initiator to be fed into the reaction vessel with the reaction mixture in a comparable time period (although with a lower feed rate). Although it is not necessary, it is preferred to add heat (to raise the temperature of the emulsion to about 80° C.) to aid polymerization.

Once the seed mixture is formed, the main portion of the unreacted monomer emulsion is then introduced along with more initiator. At this stage, the amount of initiator used is not critical, and generally consists of about 0.02–1.0% of the unreacted emulsion, and preferably, about 0.04 to 0.08% of the unreacted emulsion. Once the reaction is complete, an initiator is further added to the reacted polymer emulsion. This initiator should be hydrophobic. Such an initiator can be absorbed by the reacted polymer, and will serve to initiate polymerization in the center of the cores, where the hydrophilic initiator could not reach. Suitable initiators include t-butyl hydrogen peroxide and sodium sulfoxylate formaldehyde.

A greater degree of crosslinking may be desirable under certain circumstances since greater crosslinking provides resistance to dissolution at higher pH values. Thus where a higher pH will be used when loading the core with metal, more crosslinking agent should be included when producing the core. Other crosslinking agents can also be used in place of ALMA. Usually only one crosslinking agent is used in any one composition. Other monomers capable of providing sites for crosslinking include divinyl benzene (DVB) and acetylacetoxyethylmethacrylate (AAEM) as well as other well known crosslinking agents.

The next step in the process is to load a suitable metal onto the core material. Any suitable metal can be used. Gadolinium is often the metal of choice for MRI image enhancing agents, although any suitable paramagnetic metal may be used. Barium or other material may be used for x-ray enhancing agents. The procedure for loading metal onto the core material is as follows. The emulsion of core material from previous steps is mixed with deionized water. Since the core contains polymerized acid monomer, the emulsion will be acidic.

To the emulsified core is added ammonium hydroxide (or other suitable base) to raise the pH of the emulsion. The pH desired depends on the level of loading attempted, but generally a pH below 7 is desirable. Preferably, the pH should be below 6. If the pH of this loading step is too high, it will be difficult to form a shell over the core in later steps. Although the pH cannot be too high, in order not to inhibit shell formation, it cannot be too low either. The higher the pH, the higher the possible metal loading. If the pH is too low, there will be relatively few binding sites free, onto which to load the metal, and the metal loading level will be undesirably low.

To this is added a stoichiometric amount of metal ion. The metal can be introduced with any suitable anion. In the case of gadolinium, Gd (III) nitrate or Gd (III) chloride solution is normally used. The salt dissociates and the metal binds to the free acid portions of the resin cores. As the salt is introduced, the pH of the mixture should rise. As this happens, additional base should be added to maintain the desired pH. If the pH drops too low, the metal will become unbound from the core.

In order to use a stoichiometric amount of metal ion, it is necessary to know the metal binding capacity of the core, as well as the amount of core to be used. Any appropriate analytical method may be used, but the following method is offered as one useful way of analyzing the material. Inductively coupled plasma (ICP) may be used to determine the metal binding capacity of the resin at the intended pH. The metal ion binding capacity will change with pH, so it is important this test be run at the same pH as that intended for use when adding the metal. Thereafter, a metal salt solution is prepared having an amount of metal calculated to react with a certain quantity of resin (for instance, 100 grams resin). The solution is then tested using ICP to determine the exact quantity of Gd in solution. The amount of resin needed is then back-calculated. A suitable quantity of emulsion is then dispensed and diluted to approximately 20% solids. The diluted emulsion is then pH adjusted using a suitable base (preferably $NH_4OH$), and the metal solution is added.

To form a shell on the loaded core, a typical emulsion reaction is used. A reaction kettle is charged with deionized water. As with the formation of the core, the amount of water used will depend on the amount of emulsion to be made, and the acid content of the monomers.

The monomer mixture used for forming the shell consists of monomers taken from the list of those used for forming the core. However, in most or all cases, the composition of the shell will differ from that of the core. The acid monomer content of the emulsion used for forming the shell should be as low as possible, and certainly lower than that used for forming the core. Nevertheless, the incorporation of the acid in the shell is required for electrostatic stabilization of the particles. However, incorporation of acid in the shell creates channels which allow gadolinium to migrate from the core out through the shell. If the pH of the emulsion used for forming the shell is too low, hydronium ions will displace the metal from the core, reforming the acid core. Furthermore, the composition of the monomer mix for forming the shell should be compatible with the loaded core in surface tension. The loading of the core and the pH change of the core affects its surface tension. Therefore, the composition of the shell must be changed to achieve compatibility of surface tension in the core-shell system.

Accordingly, the monomer mix used to form the shell may have up to 15% acid monomer, but less than 10% is preferred. The acid monomer forms channels through which the loaded metal may migrate out of the shell, although it helps to stabilize the emulsion particles and prevents gelling. Therefore, too much acid monomer is also undesirable. There is a delicate need to use a shell which is compatible with the core surface (i.e. by minimizing the interfacial surface energy between the two surfaces. When this interfacial energy is not minimal, phase separation occurs to give a raspberry-type morphology. The essence of incorporation of the correct amount of hydrophilic functionality in the shell is to minimize the interfacial energy between the periphery of the core-shell system and the aqueous medium. Further, the acidic environment of the shell-forming monomer mix will allow leaching of the metal prior to shell formation. Thus the minimum amount of acid monomer needed for a continuous shell should be used. Shell thickness should be between 1 and 50 nanometers, preferably 5–30 nm.

EXAMPLES

Example 1

Weak Acid Emulsion Core with Ethyl Acrylate

A monomer emulsion was made from a mixture of 200 g deionized water, 8.13 g of 28% w/w solids ammonium lauryl sulfate (ALS), 90.0 g ethyl acrylate (EA), 90.0 g methacrylic acid (MAA), and 7.5 g allyl methacrylate (ALMA) in a bottle. A reaction kettle was then prepared with 150 g deionized water, 34.0 g of the monomer emulsion, and 0.04 g ammonium persulfate in one ml deionized water. The reaction kettle was heated to 80° C. while being purged with nitrogen. The rest of the monomer emulsion above and 32 g of a solution containing 0.20 g ammonium persulfate (APS) in deionized water were fed into the reaction flask (80° C.) at 4.0 g/min and 0.35 g/min respectively. At the end of the feed, the temperature of the reaction flask was cooled to 75° C., and then a solution of 0.10 g t-butyl hydroxy peroxide (t-BHP) in 1 ml of deionized water was added. The reaction was cooled further to 55° C. To this was added a solution of 0.060 g sodium sulfoxylate formaldehyde (SSF) in 2 ml of deionized water. The reaction was cooled to ambient temperature and the emulsion was filtered through 325 and 100 mesh sieves respectively to yield a polymer emulsion having an average particle size of 100 nm.

Example 2

Lower Loading of Weak Acid Ethyl Acrylate Core—pH 7

265.84 g of emulsion (from example 1–27.5% solids) was mixed with 200 g deionized water and 10% ammonium hydroxide, to produce a mixture having pH 7. To this was added dropwise, 133 g of a Gd (III) nitrate, hexahydrate solution (54,924 ppm in deionized water). The pH of the mixture was monitored and adjusted to 7 with ammonium hydroxide through out the test, whenever necessary, during the addition of salt solution. Stirring was continued for 30 minutes at the end of salt addition. The resulting gadolinium-loaded emulsion polymer had a loading of 0.1 g Gd per gram resin. Several other samples having different concentrations of Gd were successfully prepared using this method, as follows: 0.18, 0.015, 0.005, 0.045, and 0.03. These are set forth in Table I below.

Example 3

Higher Loading of Weak Acid Ethyl Acrylate Core—pH 7

265 g of emulsion (from example 1–27.5 % solids) was mixed with 200 g deionized water and 10% ammonium hydroxide, to produce a mixture having pH 7. To this was added dropwise, 255 g of a Gd (III) nitrate, hexahydrate solution (54,924 ppm in deionized water). The pH of the mixture was monitored and adjusted to 7 with ammonium hydroxide through out the test, whenever necessary, during the addition of salt solution. Stirring was continued for 30 minutes at the end of salt addition. The resulting gadolinium-loaded emulsion polymer had a loading of 0.20 g Gd per gram resin. Transmission electron microscopy (TEM) study showed that this encapsulated loaded core had a raspberry morphology, indicating that the shell was not continuous.

Example 4

Loaded Weak Acid Ethyl Acrylate Core (LC1.2)- pH 5

265.84 g of emulsion (from example 1–27.5 % solids) was mixed with 200 g deionized water and 10% ammonium hydroxide, to produce a mixture having pH 5. To this was added dropwise, 59.85 g of a Gd (III) nitrate, hexahydrate solution (54,924 ppm in deionized water). The pH of the mixture was monitored and adjusted to 5 with ammonium hydroxide through out the test, whenever necessary, during the addition of salt solution. Stirring was continued for 30 minutes at the end of salt addition. The resulting gadolinium-loaded emulsion polymer had a loading of 0.045 g Gd per gram resin.

Example 5

Encapsulation of Lower Loaded Weak Acid Ethyl Acrylate Core with Shell 1

The material resulting from Example 4 was encapsulated by forming a shell around the gadolinium-loaded core material (loading rate of 0.045 g Gd/g core resin). The procedure was as follows.

A reaction kettle was loaded with 200 g deionized water, 3.0 g 23% sodium benzyl laurate (siponate DS-4), 0.1 g ammonium persulfate in 2 ml deionized water, 0.2 g sodium carbonate in 3 g of deionized water, and 200 g of the loaded core from Example 4 (10.1% solids). The kettle was heated to 80° C. while being purged with nitrogen.

A monomer emulsion was then prepared with 20 g deionized water, 0.3 g of 23% sodium benzyl laurate (siponate DS-4), 1.48 g styrene, 5.8 g EA, and 0.66 g MAA. Into this emulsion were fed simultaneously 0.074 g ALMA at 1 g per min., and 0.4 g APS (in 25 g deionized water) at 0.2 g per min. At the end of the feeds, the temperature of the reaction flask was cooled to 75° C. To this was added 0.010 g t-BHP in 1 ml of deionized water. The reaction was cooled further to 55° C., and 0.020 g SSF in 2 ml of water was added. The reaction was cooled to ambient temperature and the emulsion (average particle size of 130 nm) was filtered through 325 and 100 mesh sieves respectively.

Transmission electron microscopy study on the resulting material showed the resulting loaded, encapsulated resin to have a core-shell morphology.

Example 6

Encapsulation of Lower Loaded Weak Acid Ethyl Acrylate Core with Shell 2

The material resulting from Example 4 was again encapsulated by forming a shell around the gadolinium-loaded core material (loading rate of 0.045 g Gd/g core resin). The procedure was as follows.

A reaction kettle was loaded with 200 g deionized water, 3.0 g 23% sodium benzyl laurate (siponate DS-4), 0.1 g ammonium persulfate in 2 ml deionized water, 0.2 g sodium carbonate in 3 g of deionized water, and 200 g of the loaded core from Example 4 (10.1% solids). The kettle was heated to 80° C. while being purged with nitrogen.

A monomer emulsion was then prepared with 20 g deionized water, 0.3 g of 23% sodium benzyl laurate (siponate DS-4), 1.48 g styrene, 5.8 g EA, 3.18 g BA, 0.4 g MAA. Into this emulsion were fed simultaneously 0.2 g ALMA at 1 g per min., and 0.4 g APS (in 25 g deionized water) at 0.2 g per min. At the end of the feeds, the temperature of the reaction flask was cooled to 75° C., and then 0.010 g t-BHP in 1 ml of deionized water was added. The reaction was cooled further to 55° C., and 0.020 g SSF in 2 ml of water was added. The reaction was cooled to ambient temperature and the emulsion (average particle size of 130 nm) was filtered through 325 and 100 mesh sieves respectively.

Example 7

Weak Acid Emulsion Core with Butyl Acrylate

A monomer emulsion was made from a mixture of 200 g deionized water, 1.13 g of 28% w/w solids ALS, 86.25 g butyl acrylate (BA), 93.75 g MAA, and 7.5 g ALMA. A reaction kettle was then prepared with 250 g deionized water, 34.0 g of the monomer emulsion, and 0.06 g ammonium persulfate in one ml deionized water. The reaction kettle was heated to 80° C. while being purged with nitrogen. The rest of the monomer emulsion above and 32 g of a solution containing 0.20 g APS in deionized water were fed into the reaction flask (80° C.) at 4.0 g/min and 0.35 g/min respectively. At the end of the feed, the temperature of the reaction flask was cooled to 75° C., and then a solution of 0.10 g t-butyl hydroxy peroxide (t-BHP) in 1 ml of deionized water was added. The reaction was cooled further to 55° C. To this was added a solution of 0.060 g SSF in 2 ml of deionized water. The reaction was cooled to ambient temperature and the emulsion was filtered through 325 and 100 mesh sieves respectively to yield a polymer emulsion having an average particle size of 110 nm

Example 8

Loaded Weak Acid Butyl Acrylate Core—pH 5

265.84 g of emulsion (from Example 7–27.5% solids) was mixed with 200 g deionized water and 10% ammonium hydroxide, to produce a mixture having pH 5. To this was added dropwise, 59.85 g of a Gd (III) nitrate, hexahydrate solution (54,924 ppm in deionized water). The pH of the mixture was monitored and adjusted to 5 with ammonium hydroxide throughout the test, whenever necessary, during the addition of salt solution. Stirring was continued for 30 min. at the end of salt addition. The resulting gadolinium-loaded emulsion polymer had a loading of 0.045 g Gd per gram resin.

Example 9

Loaded Weak Acid Butyl Acrylate Core—pH 7

265.84 g of emulsion (from Example 7–27.5% solids) was mixed with 200 g deionized water and 10% ammonium hydroxide, to produce a mixture having pH 7. To this was added dropwise, 199.5 g of a Gd (III) nitrate, hexahydrate solution (54,924 ppm in deionized water). The pH of the mixture was monitored and adjusted to 7 with ammonium hydroxide throughout the test, whenever necessary, during the addition of salt solution. Stirring was continued for 30 min. at the end of salt addition. The resulting gadolinium-loaded emulsion polymer had a loading of 0.15 g Gd per gram resin.

Example 10

Encapsulation of Loaded Core from Example 9

The material resulting from Example 9 was encapsulated by forming a shell around the gadolinium-loaded core material (loading rate of 0.15 g Gd/g core resin). The procedure was as follows.

A reaction kettle containing 50 g deionized water, 0.04 g ammonium persulfate in 2 ml deionized water, and 200 g of the loaded core was heated to 80° C. while purging with nitrogen. A monomer emulsion was then prepared with 60 g deionized water, 2.0 g commercially available 23% sodium benzyl laurate, 4.16 g styrene, 5.3 g EA, 3.18 g BA, and 0.4 g MAA. Into this emulsion were fed simultaneously 0.2 g ALMA at 1 g per min., and 0.4 g APS (in 25 g deionized water) at 0.2 g per min. At the end of the feeds, the temperature of the reaction flask was cooled to 75° C. To this was added 0.010 g t-BHP in 1 ml of deionized water. The reaction was cooled further to 55° C., and 0.020 g SSF in 2 ml of water was added. The reaction was cooled to ambient temperature and the emulsion (average particle size of 150 nm) was filtered through 325 and 100 mesh sieves respectively.

Transmission electron microscopy study on the resulting material showed the resin to have a core-shell morphology.

Example 11

Strong Acid Emulsion Core

A monomer emulsion was prepared by stirring vigorously under a nitrogen atmosphere, 370 g deionized water, 48.2 g of the sodium salt of an alkyl aryl polyether sulfonate surface-active agent containing 28% solids, 348.8 grams styrene, and 51.2 g of commercial-grade divinylbenzene (54.7% divinylbenzene, balance essentially ethylvinylbenzene). An aqueous initiator solution was prepared by dissolving 2.0 g of potassium persulfate in 100 g of deionized water, and 50 g of the monomer solution was added to the initiator solution. The mixture was stirred to develop a one inch vortex and headed to 70° C. under a nitrogen atmosphere. Once the polymerization began, as evidenced by a sudden decrease in opacity, the remaining monomer emulsion was added over a period of 1.5 hours. The temperature was held at 70° C. for one hour after the addition was completed. The polymer emulsion was cooled to room temperature and filtered through cheesecloth. The emulsion polymer was then sulfonated to produce a strong acid core.

Example 12

Loaded Strong Acid Core

The strong acid sulfonated emulsion core from Example 11 (average particle size of 230 nm) was loaded with gadolinium ions at a capacity of 0.25 g Gd per gram resin by using the method of Example 9. The resulting material was then encapsulated according to the procedure of Example 10.

Example 13

Anhydride Emulsion Core

A kettle was charged with deionized water (265.19 g) and LDF-2247 seed (13.15 g) and heated to 85° C. Ammonium persulfate (0.08 g in 2.50 g deionized water) was added to the kettle. A monomer emulsion was prepared from 100.95 g deionized water, 9.45 g Sipon L-22–28% solids, 65.43 g ethyl acrylate, 24.45 methyl methacrylate, 38.70 g methacrylic anhydride and 5.23 g allyl methacrylate. This emulsion was fed into a reactor at 3.90 g/minute, along with a cofeed catalyst of ammonium persulfate (0.16 g in 11.0 g deionized water) at a rate of 0.18 g/minute. The mixture was stirred for 30 minutes, and cooled to 65° C. To this was added t-BHP (0.38 g in 2.5 g water) and the reaction allowed to proceed for 20 minutes. Next was added $Fe_2SO_4.7H_2O$ (1.50 g) and SSF (0.19 g) in 7.5 g water, and the reaction was allowed to proceed for 20 minutes, after which the emulsion was cooled to ambient temperature and filtered through a 325 mesh screen.

The resulting anhydride core (184.5 g), was then mixed with water (245.4 g), ammonia—28% (0.5 g in 10 g water), and dimethylaminopropylamine (13.46 g, 93.4 mmol). This was added to a reaction kettle and heated to 90° C. with stirring for 6 hours. The kettle was cooled to ambient temperature and the emulsion was filtered through a 325 mesh screen. Note that other experiments substituted 4-(3-aminopropyl)morpholine (13.46 g, 93.4 mmol) or iminodiacetic acid (4.14 g, 31.1 mmol) for the dimethylaminopropylamine. Any other suitable polyamine can be substituted instead, including diamines, and EDTA and morpholine analogs.

The opened anhydride core can be loaded and encapsulated as set forth in the examples above. However, it should be noted that a shell may not be necessary for sequestration of the gadolinium ions if the binding of the ions by the core is sufficiently strong.

The Gd loaded nanoparticles (and some particles without loading) outlined above have been examined to determine their effect on $T_1$ (transverse or spin-lattice relaxation times). The $T_1$ values were measured at 400 MHz using the standard inversion recovery pulse sequence. The samples were placed in 5 mm NMR tubes with no deuterated solvent to lock the field. In order to avoid radiation dumping from the strong water signal during the delay times, the probe was mismatched. About ten delay ($\tau$) values were used for each $T_1$ measurement. The resulting experimental intensities versus delay times for each sample was fit using a single exponential function. The standard deviations were all on the order of 0.0001. Results of the NMR experiments for the metal latexes are compared with a commercial standard (Prohance®, available from Bracco Diagnostics of Princeton, N.J.) in Table 1. Prohance® is a commercial grade Gd-chelate contrast agent which is currently approved for medical imaging.

TABLE 1

NMR relaxation times $T_1$

| Sample | g Gd/g polymer | g Gd/l | $T_1$ (ms) |
| --- | --- | --- | --- |
| ultrapure $H_2O$ | | | 2200 |
| 10% Latex polymer from Example 1 | 0 | 0 | 2054 |
| 10% Latex polymer from Example 2 | 0 | 0 | 2630 |
| 2 mM Prohance ® | 0.28$^a$ | 0.31 | 20 |
| 10 mM Prohance ® | 0.28$^a$ | 1.57 | 4 |
| 100 mM Prohance ® | 0.28$^a$ | 15.7 | 0.3 |
| Core prepared according to Example 2, with Gd | 0.18 | 11.4$^b$ | 1.6 |
| Core prepared according to Example 2, with Gd | 0.1 | 8.0$^b$ | 2.3 |
| Core prepared according to Example 2, with Gd | 0.015 | 1.2$^b$ | 36 |
| Core prepared according to Example 2, with Gd | 0.005 | 0.4$^b$ | 97 |
| Core prepared according to Example 2, with Gd | 0.045 | 3.6$^b$ | 11 |
| Core prepared according to Example 2, with Gd | 0.03 | 2.4$^b$ | 16 |
| Core-Shell polymer 1 from Example 5 | 0.031 | 1.98 | 22 |
| Core-Shell polymer 2 from Example 6 | 0.026 | 1.48 | 29 |

$^a$Prohance metal loading relative to polycarboxylate ligand.
$^b$Estimate based on average value of 8% solid content for core polymer.

Table 1 shows that these materials provide significant relaxivity, and should be useful as contrast-enhancing agents. The commercial standard (Prohance®) is able to reduce $T_1$ by two to three orders of magnitude, depending on concentration. The metal loaded polymers of the present invention have a similarly dramatic effect. Metal loadings are reported in Table 1 as a ratio of weight of Gd per weight of polymer (g Gd/g polymer). At the 0.1 g Gd/g polymer loading $T_1$ is reduced by three orders of magnitude. Even at very low loadings of 0.005 g Gd/g polymer, the $T_1$ is reduced from 2200 ms for pure water to only 97 ms. For comparison, the metal load for Prohance is 0.28 g Gd/g ligand. This shows conclusively that the Gd loaded polymers of the present invention very effectively reduce the $T_1$ of water, and therefore provide MRI contrast.

In order to follow the change in $T_1$ with respect to total metal concentration, approximate metal concentrations were calculated for the polymers and Prohance®. These are reported in Table 1, with the $T_1$ values.

In order to further assess the potential of these materials as contrast agents, imaging experiments were carried out using Buffalo rats. In a typical experiment 0.5–0.7 ml of the contrast agent of Example 5 was administered via the tail vein. Imaging began approximately 7 minutes after administration. Full scans of the rat body were taken at approximately 4 minute intervals up to 45 minutes post injection. Pre- and post-contrast images of the heart showed that the contrast agent led to very significant enhancement of the intravascular space. The heart chamber was brightly lit by the contrast agent as were all of the major arteries leading into or out of the heart. Further it is possible to image essentially any other large veins or arteries in the animal post-contrast. Images of the kidneys show significant accumulation of the contrast agent in the kidneys even 7 minutes post injection. Interestingly the kidney was one organ where the agent was seen to be exiting the intravascular space at any significant rate.

In addition these paramagnetic agents were evaluated as oral contrast agents. Two to three milliliters of three different concentrations of the agent of Example 5 were administered orally to each of three different Buffalo rats. The concentrations were dilutions (1:1;1:10;1:100) of the agent shown in Example 5. Full body scans of the rats were started 2 minutes post administration and were continued at about 2 minute intervals for up to one hour. A comparison of these images showed that the 1:10 dilution was most effective. The most significant observation was that the gastrointestinal tract was easily visualized post administration. The enhancement observed persisted over almost the full hour. The stomach and intestines were easily seen in at least two scan planes, indicating that this agent is effective as an oral contrast agent in MRI.

We claim:

1. An image enhancing agent comprising:

a polymeric core having an image-enhancing compound chemically bound thereto; and a polymeric shell surrounding said core and compound, wherein said core comprises a polymer formed from a monomer mixture comprising between 10 and 90% acid monomer, and 10 and 90% esterified monomer, and wherein said compound is a metal that binds to acidic regions in said core.

2. The agent of claim 1 wherein said metal is gadolinium.

3. The agent of claim 1 wherein said shell completely encapsulates said core.

4. The agent of claim 1 wherein said core comprises a polymer formed from a monomer mix comprising 50 to 70% acid monomer and 30–50% esterified monomer.

5. The agent of claim 4 wherein said acid monomer is at least one compound selected from the group consisting of acrylic acid, methacrylic acid, methyl methacrylate, styrene, ethyl acrylate, butyl acrylate, 2-ethylhexyl acrylate, dimethylaminoethyl methacrylate, tert-butylaminoethyl methacrylate, hydroxyethyl methacrylate, and hydroxypropyl methacrylate.

6. The agent of claim 5 wherein said monomer mix further comprises up to 10% of a cross-linking agent selected from the group consisting of allyl methacrylate (ALMA), ethylene glycol dimethacrylate (EGDMA), trimethylolpropane trimethacrylate (TMPTMA), divinyl benzene (DVB), glycidyl methacrylate, 2,2-dimethylpropane 1,3 diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, trimethylolpropane triacrylate, trimethylolpropane trimethacrylate, pentaerythritol triacrylate, trimethylolpropane triethoxy triacrylate, glyceryl propoxy triacrylate, pentaerythritol tetraacrylate, pentaerythritol tetramethacrylate, and dipentaerythritol monohydroxypentaacrylate.

7. The agent of claim 4 wherein said shell comprises a polymer formed from a monomer mixxture having up to 15% acid monomer to provide hydrophilic functionality in said shell.

8. A method of generating an image comprising administering to a subject the image-enhencing agent of claim 1, and subjecting said subject to and image-forming procedure.

9. The method of claim 8 wherein said image forming procedure is an MRI procedure.

10. The method of claim 9 wherein the polymeric core of said image enhancing agent contains a polymer formed from a monomer mix comprising 50 to 70% acid monomer and 30–50% esterified monomer, and the shell of said image enhancing agent contains a polymer formed from a monomer mixture having up to 15% acid monomer to provide hydrophilic functionality in said shell.

* * * * *